United States Patent
Fu et al.

(10) Patent No.: US 11,702,383 B2
(45) Date of Patent: Jul. 18, 2023

(54) METHODS FOR PRODUCING D-α-METHYLDOPA

(71) Applicant: ImmunoMolecular Therapeutics, Inc., Woburn, MA (US)

(72) Inventors: Xing Fu, Acton, MA (US); Rajesh Shukla, North Andover, MA (US)

(73) Assignee: ImmunoMolecular Therapeutics, Inc., Woburn, MA (US)

( * ) Notice: Subject to any disclaimer, the term of this patent is extended or adjusted under 35 U.S.C. 154(b) by 9 days.

(21) Appl. No.: 17/557,472

(22) Filed: Dec. 21, 2021

(65) Prior Publication Data

US 2022/0194893 A1 Jun. 23, 2022

Related U.S. Application Data

(60) Provisional application No. 63/129,875, filed on Dec. 23, 2020.

(51) Int. Cl.
*C07C 227/02* (2006.01)
*C07C 253/30* (2006.01)
*C07C 227/18* (2006.01)

(52) U.S. Cl.
CPC .......... *C07C 227/02* (2013.01); *C07C 227/18* (2013.01); *C07C 253/30* (2013.01); *C07B 2200/07* (2013.01)

(58) Field of Classification Search
None
See application file for complete search history.

(56) References Cited

U.S. PATENT DOCUMENTS 4,187,244 A 2/1980 Hohnjec et al.
9,820,957 B2 * 11/2017 Orndorff .............. A61K 31/198

FOREIGN PATENT DOCUMENTS

| CN | 102702004 | * 10/2012 | ........... C07C 227/18 |
| CN | 102786428 A | 11/2012 | |
| CN | 103435507 | * 12/2013 | ........... C07C 227/26 |
| CN | 103804234 | * 5/2014 | ........... C07C 253/30 |

OTHER PUBLICATIONS

Machine generated English translation of CN 102786428, obtained Feb. 23, 2023 (Year: 2023).*
Rahmani-Nezhad, S. et al., "A Crystallization-Induced Asymmetric Transformation using Racemic Phenyl Alanine Methyl Ester Derivatives as Versatile Precursors to Prepare Amino Acids", J. Sciences, Islamic Republic of Iran, vol. 30, No. 1, 2019, 23-31.

* cited by examiner

*Primary Examiner* — Amy C Bonaparte
(74) *Attorney, Agent, or Firm* — Elmore Patent Law Group, P.C.; Carolyn Elmore; Edgar Harlan

(57) ABSTRACT

The present invention provides methods of synthesizing D-α-methyldopa and L-α-methyldopa.

20 Claims, No Drawings

METHODS FOR PRODUCING D-α-METHYLDOPA

RELATED APPLICATION

This application claims the benefit of U.S. Provisional Application No. 63/129,875, filed on Dec. 23, 2020. The entire teachings of the above application are incorporated herein by reference.

BACKGROUND OF THE INVENTION

Therapeutic uses have been described for both enantiomers of α-methyldopa. For example, U.S. Pat. No. 9,820,957 discloses the use of the D-enantiomer for treating autoimmune disorders, such as Type 1 diabetes and celiac disease, while the L-enantiomer is marketed for the treatment of hypertension. There is a need for improved methods for preparing both enantiomers of α-methyldopa.

SUMMARY OF THE INVENTION

The present invention provides methods of synthesizing D-α-methyldopa and L α-methyldopa. The methods of the invention provide these compounds in high overall yield and high enantiomeric purity.

In a first embodiment, the invention provides a method of producing D-α-methyldopa,

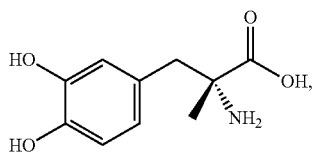

comprising the steps of:
(1-a) reacting compound 1,

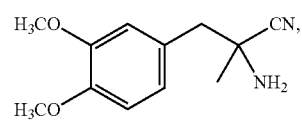

with L-tartaric acid, thereby producing compound 2,

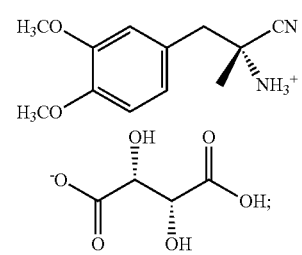

(1-b) reacting compound 2 with aqueous HCl, thereby producing compound 3,

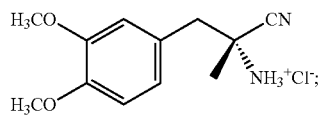

(1-c) reacting compound 3 with hydrochloric acid, thereby producing compound 4,

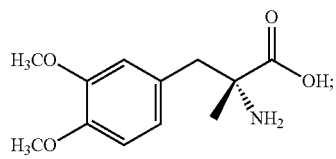

and
(1-d) reacting compound 4 with hydrobromic acid in the presence of an antioxidant to produce D-α-methyldopa.

In a second embodiment, the invention provides a method of producing D-α-methyldopa,

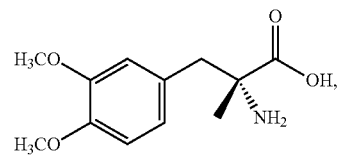 [SMILES: COc1ccc(C[C@@](C)(N)C(=O)O)cc1OC]

comprising the steps of:
(1-a) reacting compound 1,

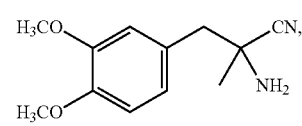

with L-tartaric acid, thereby producing compound 2,

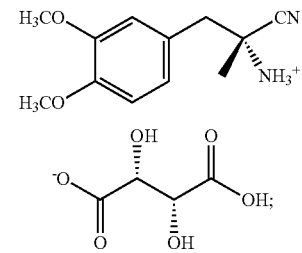

(2-b) reacting compound 2 with a chlorinating agent to produce compound 3,

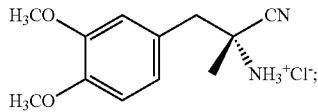

and (2-c) reacting compound 3 with hydrobromic acid in the presence of an antioxidant, thereby producing D-α-methyldopa.

In a third embodiment, the invention provides a method of producing D-α-methyldopa,

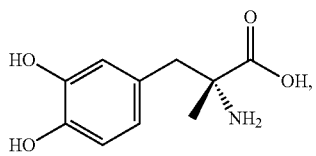

comprising the steps of:

(1-a) reacting compound 1,

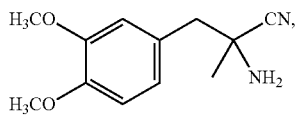

with L-tartaric acid thereby producing compound 2,

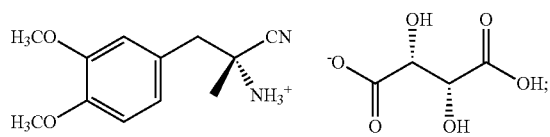

(1-b) reacting compound 2 with aqueous HCl, thereby producing compound 3,

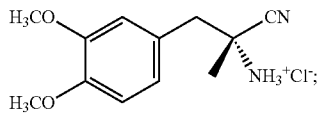

and (2-c) reacting compound 3 with hydrobromic acid in the presence of an antioxidant, thereby producing D-α-methyldopa.

It will be appreciated that the methods of the invention can be also be used for producing L-α-methyldopa by replacing L-tartaric acid in step (1-a) with D-tartaric acid.

DETAILED DESCRIPTION OF THE INVENTION

The present invention provides improved methods for producing D-α-methyldopa and L-α-methyldopa. In particular, the methods of the invention are simpler, involve fewer steps and result in higher product yields than prior art methods and provide D-α-methyldopa or L-α-methyldopa in acceptable purity, including acceptable enantiomeric purity.

In step (1-a), compound 1 reacts with L-tartaric acid (for the production of D-α-methyldopa) or D-tartaric acid (for the production of L-α-methyldopa), to produce the tartrate salt (compound 2 or its enantiomer). In certain embodiments, compound 1 is first treated with about 1 to about 1.5 molar equivalents of aqueous HCl, for example, at an HCl concentration of about 0.4 to about 1.0 M, and the mixture is agitated and filtered to remove any cyanohydrin impurity from compound 1. The tartaric acid is added, for example, in an amount of about 1.0 to 1.5 molar equivalents relative to compound 1, at a temperature preferably in the range of about 20-40° C., more preferably from about 25 to about 35° C. The mixture is treated with base, preferably a strong base such as aqueous sodium hydroxide, and preferably maintained at a temperature from about 0 to about 10° C., more preferably from about 0 to about 5° C., causing compound 2 to precipitate. The resulting reaction mixture is then worked up as is known in the art.

In step (1-b), compound 2 is reacted with aqueous HCl to produce compound 3. In certain embodiments of step (1-b), compound 2 is added to water and a water-immiscible organic solvent, such as dichloromethane. The pH of this mixture is preferably adjusted to the range of 5.5 to 7.5, more preferably 6 to 7, by addition of a base, such as aqueous ammonium hydroxide. In certain embodiments, the organic layer is separated and treated with aqueous HCl, preferably at a temperature of about 0 to about 10° C., more preferably from about 0 to about 5° C. Preferably, the aqueous HCl has a concentration of about 6 to about 12 M, about 10 to about 12 M or about 12 M. The resulting reaction mixture is then worked up as is known in the art.

In step (2-b), compound 2 is reacted with a chlorinating agent, such as thionyl chloride, PCl₅, POCl₃, PCl₃, or oxalyl chloride, to produce compound 3. A preferred chlorinating agent is thionyl chloride. In certain embodiments of step (2-b), compound 2 is combined with a hydrophilic organic solvent or a combination of hydrophilic organic solvents with an alcohol, preferably the solvent is a protic solvent such as an alcohol, for example, methanol, ethanol, or isopropanol. The chlorinating agent, such as thionyl chloride, is preferably added to this mixture in stoichiometric excess to compound 2, for example, about 2- to about 10-fold excess and preferably about 4-fold excess. The chlorinating agent, such as thionyl chloride, is preferably added under conditions which maintain the temperature of the reaction mixture under about 60° C., and preferably under about 40° C. The resulting mixture is then preferably maintained at a temperature of about 20 to about 90° C., preferably about 20 to about 80° C. and more preferably about 20 to about 40° C. The resulting reaction mixture is then worked up as is known in the art. In step (1-c), compound 3 is reacted with aqueous HCl to produce compound 4. In certain embodiments the concentration of the aqueous HCl is about 6M or greater, preferably 10-12 M and more preferably 12 M. In certain embodiments, compound 3 and the aqueous HCl are mixed, and the mixture is heated, for example, at a temperature of 30 to about 60° C., preferably about 40 to about 50° C. and more preferably about 44 to about 46° C. The resulting reaction mixture is then worked up as is known in the art.

In step (1-d), compound 4 is reacted with aqueous HBr in the presence of an antioxidant, such as phenol or a substituted phenol, for example, dihydroxybenzene, trihydroxybenzene, butylated hydroxyanisole or butylated hydroxytoluene, to produce D-α-methyldopa. Preferably the antioxidant is phenol. In certain embodiments of step (1-d), compound 4 is combined with aqueous HBr, phenol and optionally ammonium chloride. The amount of phenol is preferably about 0.25 molar equivalents relative to compound 4 or greater, such as 0.5 molar equivalents or greater, 0.75 molar equivalents or greater, 1.0 molar equivalents or greater or 1.25 molar equivalents or greater. Preferably, the amount of phenol is from 1 to 1.5 molar equivalents relative to compound 4. The aqueous HBr preferably has a concentration of 30% HBr or greater, more preferably 35-48% HBr and most preferably 48% HBr. The mixture is preferably heated, for example to a temperature of 70 to about 100° C., preferably about 80 to about 90° C. and more preferably about 84 to about 86° C. The resulting reaction mixture is then worked up as is known in the art.

In step (2-c), compound 3, preferably as the HCl salt, is reacted with aqueous HBr in the presence of an antioxidant, such as phenol or substituted phenol, for example dihydroxybenzene, trihydroxybenzene, butylated hydroxyanisole or butylated hydroxytoluene, to produce D-α-methyldopa. Preferably the antioxidant is phenol. In certain embodiments of step (2-c), compound 3 free base or the HCl salt of compound 3 is combined with aqueous HBr, phenol and optionally ammonium chloride. The amount of phenol is preferably about 0.25 molar equivalents relative to compound 3 or greater, such as 0.5 molar equivalents or greater, 0.75 molar equivalents or greater, 1.0 molar equivalents or greater or 1.25 molar equivalents or greater. Preferably, the amount of phenol is from 1 to 1.5 molar equivalents relative to compound 3. The aqueous HBr preferably has a concentration of 30% HBr or greater, more preferably 35-48% HBr and most preferably 48% HBr. The mixture is preferably heated, for example to a temperature of 70 to about 100° C., preferably about 80 to about 90° C. and more preferably about 84 to about 86° C. The resulting reaction mixture is then worked up as is known in the art.

Schemes 1-3 illustrate preferred embodiments of the methods of the invention for producing D-α-methyldopa.

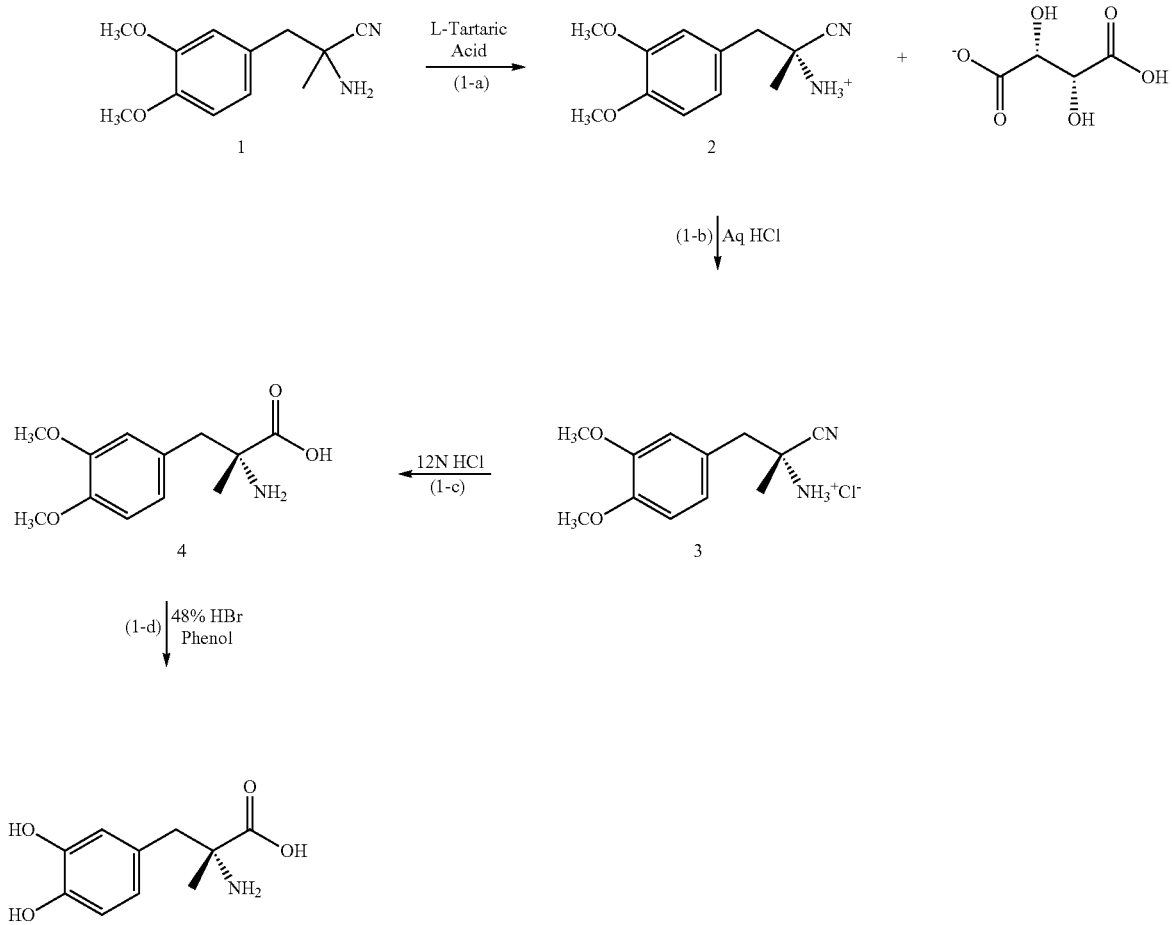

Scheme 1

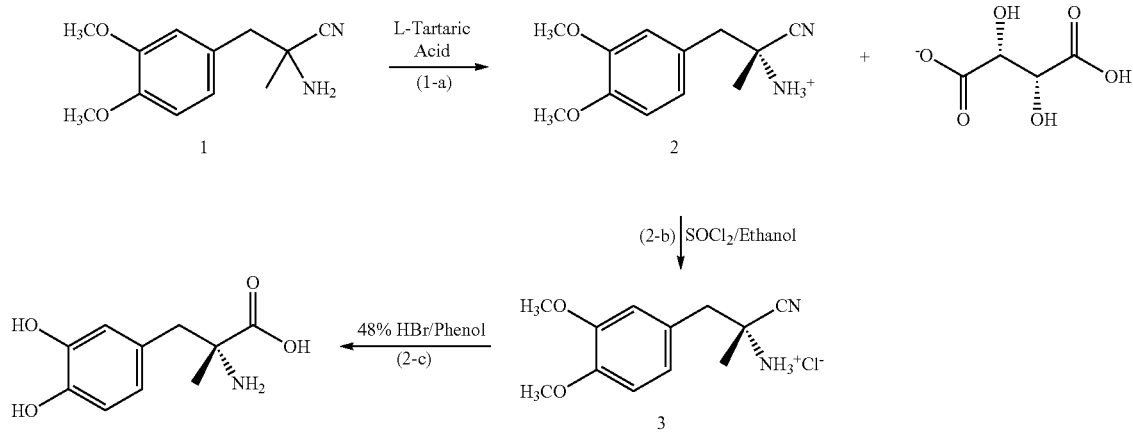

Scheme 2

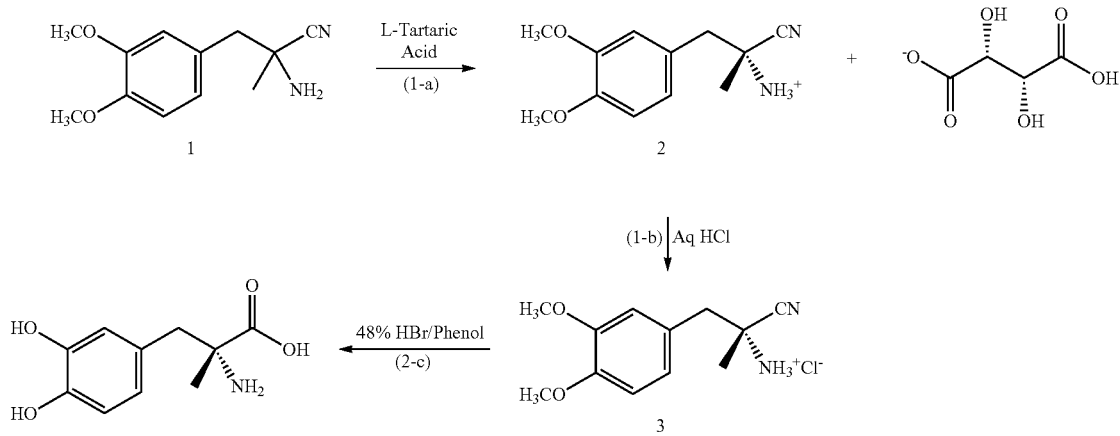

Scheme 3

It is to be understood that any of the methods of the invention for producing D-α-methyldopa can also be used to produce L-α-methyldopa by replacing L-tartaric acid in step (1-a) with D-tartaric acid. The resulting methods for producing L-α-methyldopa proceed via the enantiomers of compounds 2, 3, and 4. Such methods for producing L-α-methyldopa are also within the scope of this invention.

Exemplification

Preparation of Compound 2 (Step (1-a))

Compound 1 (3 kg, 1.0 equiv.) was charged to a 100 L RBF at 25-35° C. and 0.7 N aq. HCl (21.4 L, 1.1 equiv.) was charged to the RBF and agitated for 90 minutes The mixture was filtered (to remove cyanohydrin impurity) and the filtrate was collected and transferred to the 100 L RBF. L-(+)-Tartaric acid (2.25 kg, 1.1 equiv.) was then added to the reactor at 25-35° C. and agitated for 10 minutes. The mixture was then cooled to 0-5° C. and 3N aqueous sodium hydroxide solution (4.54 L, 1 equiv.) was slowly added to the reactor while maintaining the temperature between 0-15° C. The suspension was then agitated for 1 h at the same temperature. Acetone (6 L, 2 vol.) was added to the suspension to make it flow freely and agitated for another 1 h. The free solids were filtered and washed with cold acetone (6 L, 2 vol.) and dried under vacuum to afford 5.8 kg of compound 2 (Wet cake1) This material was combined with 3.7 kg of compound 2 (wet cake) which was obtained from another 2 kg batch. The subsequent 9.5 kg (wet cake) of compound 2 (3.7 and 5.8 kg) was charged to a 100 L RBF followed by acetone (30 L, 6 vol.) at room temperature and agitated for 1 h. The mixture was cooled to 0-10° C. and agitated for another 90 minutes. The resulting solids were filtered and washed with cold acetone (10 L, 2 vol.) and suck dried under vacuum for 30 minutes. The wet cake was transferred to the trays and air dried for 12 h to afford 3.4 kg of compound 2 as a white solid in 40% yield 3.4 kg with 98.49% (corrected for 6.23% water content by KF titration) chiral purity and 97.96%. HPLC purity.

Preparation of Compound 3 (Step (1-b))

Compound 2 (100 g, 0.27 mol) was charged in to 3 L flask, followed by D.I. water (1.5 L, 15 vol.) and dichloromethane (0.5 L, 5 vol.). The resulting mixture was cooled to 0-5° C. pH was adjusted with ~2N ammonium hydroxide solution to 6.0-7.0 and then the mixture was stirred at 0-5°

C. for 10 min. The layers were separated and then the aqueous layer was extracted with DCM (250 mL, 2.5 vol×2). The combined organic layers were washed with D.I. water (250 mL, 2.5 vol×2). The organic layer was cooled to 0-5° C. and then conc. HCl solution (40 mL, ~0.48 mol) was charged into mixture dropwise to maintain inner temp no greater than 10 C°. The resulting mixture was stirred at 0-5° C. for 1 h, solid was observed in the mixture. The mixture was kept at 0-5° C. overnight. DCM was distilled under reduced pressure to ~200 mL (2.0 vol.) and then chased with toluene (500 mL, 5 vol×2) to a volume of ~200 mL (2.0 vol.). Toluene (250 mL) was charged into the residue to form a slurry. Solid was collected by filtration and then rinsed with toluene (100 mL, 1.0 vol×2). HPLC analysis of the filtrate indicated that no product was present. The wet cake was dried at 50±5° C. under reduced pressure overnight to give the product (51.9 g, 202 mmol). HPLC analysis for this sample indicated that the chemical purity was 98.9% AUC. The isolated yield of Compound 3 adjusted for water content (by Karl Fischer titration) of starting material was 79.8%.

Preparation of Compound 3 (Step (2-b)) (Example 1)

Compound 2 (5.0 g, 13.5 mmol) was charged to a 250 mL flask, followed by ethanol (50 mL, 10 vol.). Thionyl chloride (4.0 mL, 6.55 g, 55 mmol, 4.08 eq) was charged dropwise to maintain inner temperature below 40° C. After addition, the mixture was heated to 75±5° C. and then stirred at the same temperature for 2 h. The mixture was cooled to room temperature overnight. Ethanol was removed by concentration in vacuo to ~5 mL (1 vol.). MTBE (50 mL, 10 vol.) was charged into residue to precipitate the solid, slurry was stirred at 25±5° C. for 1 h. Solid was collected by filtration and then rinsed with MTBE (10 mL, 2 vol.) twice. A white solid (2.71 g) was obtained after the wet cake was dried at 45±5° C. for 18 h. The overall isolated yield was 83.5% after adjustment with 6.23% w/w of water content in compound 2.

Preparation of Compound 3 (Step (2-b)) (Example 2)

Ethanol (200 mL, 8 vol.) was charged into 500 mL 3-necked flask and then thionyl chloride (5 mL, 1.03 eq.) was added into ethanol dropwise to maintain inner temperature below 35° C. Compound 2 (25 g, 67.5 mmol, 1.0 eq. with water content at 6.23% w/w) was charged into flask, followed by ethanol (50 mL, 2 vol.). Thionyl chloride (14.8 mL, 3.05 eq.) was charged into mixture dropwise to maintain an inner temperature below 45° C. The resulting reaction mixture was stirred at 25±5° C. (target 22° C.) for 18 h. The mixture was cooled to room temperature and then ethanol was removed by distillation under reduced pressure to ~38 mL (1.5 vol.). Ethyl acetate (125 mL, 5 vol.)×2 was used to chase ethanol by azeotrope to ~38 mL (1.5 vol.) and then ethyl acetate (213 mL, 8.5 vol) was charged into residue to total 10 vol. The resulting slurry was stirred at 25±5° C. for 1 h. Solid was collected by filtration and then rinsed with ethyl acetate (25 mL, 1 vol.) twice. A white solid (13.8 g) was obtained after the wet cake was dried below 40° C. for 24 h. The isolated yield was 85% after adjustment with water content (6.23% w/w) in compound 2.

Preparation of Compound 4 (Step (1-c))

Compound 3 (2.5 g, 9.74 mmol) was charged into three necked flask (150 mL), followed by 12N HCl solution (50 mL). The resulting mixture was heated to 45±5° C. and stirred at 45±5° C. for 19 h. An aliquot was pulled for HPLC in-process analysis. HPLC result indicated that starting material was present at 39.5 AUC level. The above reaction mixture was heated at 45±5° C. for additional 48 h. The reaction mixture was concentrated in vacuo to give an off-white solid. The solid was dried at room temperature under reduced pressure for 44 h to give Compound 4 with 1 eq. of ammonium chloride (3.1 g). The isolated yield is 96.7%.

Preparation of D-α-methyldopa (Step (1-d))

Compound 4 with 1 eq. of ammonium chloride (3.0 g, 9.1 mmol) was charged into 20 mL reaction vial, followed by phenol (1.7 g, 18.2 mmol, 2.0 eq) and 48% HBr solution (60 mL, 89.4 g, 530.3 mmol). The mixture was heated at 85±5° C. Samples were pulled for HPLC assay. Results of HPLC analysis indicated that reaction reached completion after 10 h. The mixture was cooled to room temperature and then was concentrated in vacuo to remove HBr solution at a bath temperature 60° C. under reduced pressure. HBr solution (50 mL) was removed during the evaporation. The residue was chased with toluene (100 mL×2). HPLC analysis of distillate and residue indicated that phenol was removed from residue during the evaporation. Water (4 mL) was added to obtain a clear solution. The resulting solution was cooled to 0-5° C. The pH was adjusted with 2.0 N ammonium hydroxide solution. After 2.0 N ammonium hydroxide (25 mL) was added the pH of the mixture was still 1.0. The mixture was concentrated in vacuo to a volume of ~12 mL and then cooled to 0-5° C. Ammonium hydroxide solution (28-29%) and conc. HCl solution were used for adjustment of pH to 4.5. Solid precipitated and was collected by filtration, followed by a rinse with D. I. water (4 mL×2). The wet solid (2.1 g) was dried at room temperature under reduced pressure for 4 days to give the product (1.38 g). The isolated yield was 71.8%.

Preparation of D-α-methyldopa (Step (2-c))

Compound 3 HCl salt (50 g, 195 mmol) and phenol (18.4 g, 195 mmol, 1.0 eq.) were charged into 1000 mL 3 necked flask, followed by 48% HBr solution (500 mL, 744.6 g, 10 vol.). The mixture was heated at 85±5° C. Results of HPLC analysis of an aliquot indicated the reaction reached to completion after 44 h at 85±5° C. without intermediates being observed. The mixture was cooled to room temperature and then concentrated under reduced pressure to remove HBr solution at temperature below 60° C. to ~100 mL (2.0 vol.). The residue was chased with deionized (DI) water (250 mL, 5 vol.) twice. Then residue was stored at room temperature overnight. D. I. Water (150 mL, 3 vol.) was added to a total volume ~250 mL and then a clear solution was obtained. The resulting solution was cooled to 0-5° C. and the pH was adjusted with 28-29% ammonium hydroxide solution and conc. HCl solution to pH 6 and solid was precipitated. Additional D.I. water (100 mL) was added into mixture to form a filterable slurry. The solid was collected by filtration, followed by rinsing with cold D. I. water (0-5° C.) (50 mL, 1.0 vol.×2). The wet solid (66 g) was dried at room temperature under reduced pressure for 11 days to constant weight (39.9 g). The isolated yield was 86.0% (99.9% pure).

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

What is claimed is:

1. A method of producing D-α-methyldopa, comprising the steps of:
   (1-a) reacting compound 1,

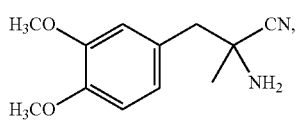

with L-tartaric acid, thereby producing compound 2,

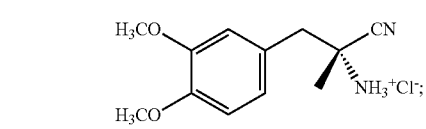

(1-b) reacting compound 2 with aqueous HCl, thereby producing compound 3,

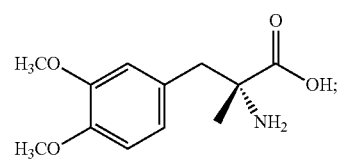

(1-c) reacting compound 3 with hydrochloric acid, thereby producing compound 4,

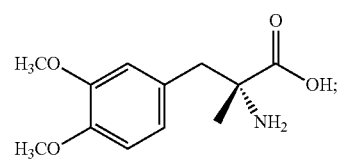

and
   (1-d) reacting compound 4 with hydrobromic acid in the presence of an antioxidant to produce D-α-methyldopa.

2. The method of claim 1, wherein the antioxidant is phenol or substituted phenol.

3. The method of claim 2 wherein the antioxidant is phenol, dihydroxyphenol, trihydroxyphenol, butylated hydroxyanisole or butylated hydroxytoluene.

4. The method of claim 1, wherein the antioxidant is phenol.

5. A method of producing D-α-methyldopa, comprising the steps of:
   (1-a) reacting compound 1,

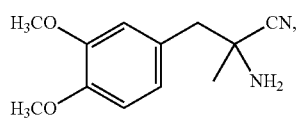

with L-tartaric acid, thereby producing compound 2,

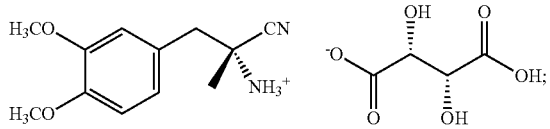

(2-b) reacting compound 2 with a chlorinating agent to produce compound 3,

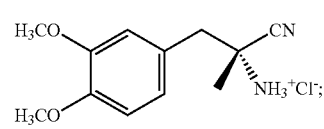

and
   (2-c) reacting compound 3 with hydrobromic acid in the presence of an antioxidant, thereby producing D-α-methyldopa.

6. The method of claim 5, wherein the antioxidant is phenol or substituted phenol.

7. The method of claim 5, wherein the antioxidant is phenol.

8. The method of claim 5, wherein the chlorinating agent is thionyl chloride, phosphoryl chloride, phosphorus trichloride, phosphorus pentachloride or oxalyl chloride.

9. The method of claim 8, wherein the chlorinating agent is thionyl chloride.

10. A method of producing D-α-methyldopa, comprising the steps of:
    (1-a) reacting compound 1,

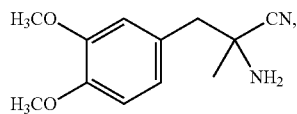

with L-tartaric acid, thereby producing compound 2,

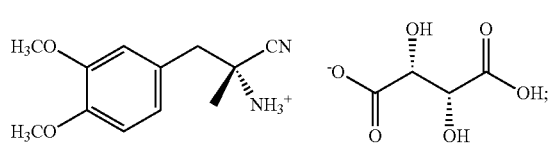

(1-b) reacting compound 2 with aqueous HCl, thereby producing compound 3,

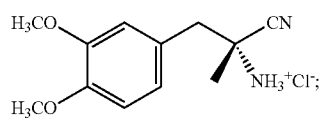

and
(2-c) reacting compound 3 with hydrobromic acid in the presence of antioxidant thereby producing D-α-methyldopa.

11. The method of claim 10, wherein the antioxidant is phenol or a substituted phenol.

12. The method of claim 11, wherein the antioxidant is phenol, dihydroxyphenol, trihydroxyphenol, butylated hydroxyanisole or butylated hydroxytoluene.

13. The method of claim 12, wherein the antioxidant is phenol.

14. The method of claim 5, wherein in step (2-c), compound 3 is reacted with aqueous HBr and phenol in the presence of ammonium chloride.

15. The method of claim 14, wherein the amount of phenol is about 1 to about 2 molar equivalents relative to compound 3.

16. The method of claim 14, wherein the aqueous HBr has a concentration of 30% HBr or greater.

17. The method of claim 1, wherein in step (1-a), the amount of tartaric acid is about 1.0 to about 1.5 molar equivalents relative to compound 1 and the reaction is conducted at a temperature from about 20 to about 40° C.

18. The method of claim 4, wherein in step (1-d), compound 4 is reacted with aqueous HBr and phenol in the presence of ammonium chloride.

19. The method of claim 18, wherein the amount of phenol is about 1 to about 2 molar equivalents relative to compound 4.

20. The method of claim 18, wherein the aqueous HBr has a concentration of 30% HBr or greater.

* * * * *